United States Patent [19]

Schrier et al.

[11] Patent Number: 5,733,556
[45] Date of Patent: Mar. 31, 1998

[54] NEWCASTLE DISEASE VIRUS COMBINATION VACCINE

[75] Inventors: Carla Christina Schrier; Heinrich Dieter Lütticken, both of Boxmeeer, Netherlands

[73] Assignee: Akzo Nobel N.V., Arnhem, Netherlands

[21] Appl. No.: 730,137

[22] Filed: Oct. 15, 1996

[30] Foreign Application Priority Data

Oct. 18, 1995 [EP] European Pat. Off. ............. 95202810

[51] Int. Cl.$^6$ .................... A61K 39/17; A61K 39/12; C12N 15/00; C12N 7/00
[52] U.S. Cl. .................... 424/214.1; 424/199.1; 424/186.1; 424/204.1; 424/229.1; 424/232.1; 424/816; 435/235.1; 435/320.1
[58] Field of Search .................... 424/186.1, 204.1, 424/422, 232.1, 89, 199.1, 214.1, 229.1, 816; 435/235.1, 320.1

[56] References Cited

U.S. PATENT DOCUMENTS

| | | | |
|---|---|---|---|
| 5,118,502 | 6/1992 | Glisson et al. | 424/89 |
| 5,250,298 | 10/1993 | Gelb, Jr. | 424/214.1 |
| 5,538,733 | 7/1996 | Emery et al. | 424/472 |

FOREIGN PATENT DOCUMENTS

| | | |
|---|---|---|
| 292293 | 11/1988 | European Pat. Off. . |
| 0351908 | 1/1990 | European Pat. Off. . |
| WOA 9006131 | 6/1990 | WIPO . |
| WOA 9015623 | 12/1990 | WIPO . |
| WOA 9419015 | 9/1994 | WIPO . |

OTHER PUBLICATIONS

R. Morgan et al., *Avian Disease*, 37:1032–1040, 1993.
R. Morgan et al., *Avian Disease*, 36:858–870, 1992.
I. Roitt, *Encyclopedia of Immunology*, 1992, Academic Press, 1203–1206, 1992.
P. Sondermeijer et al., *Vaccine*, 11:3:349–358, 1993.
Kamiya et al, 1944, Virus Res., vol. 32, pp. 373–379.
Cosset et al, 1991, Virology; vol. 185, pp. 862–866.

*Primary Examiner*—Marian C. Knode
*Assistant Examiner*—Ali Salimi
*Attorney, Agent, or Firm*—Sharon N. Klesner; Mary E. Gormley

[57] ABSTRACT

The present invention provides a combination vaccine for use in the protection of poultry against ND comprising an expression system, such as a virus vector, expressing a NDV immunogenic protein, and a live NDV vaccine strain. It is demonstrated that such a combination vaccine affords good local and systemic protection.

12 Claims, No Drawings

NEWCASTLE DISEASE VIRUS COMBINATION VACCINE

FIELD OF THE INVENTION

The present invention is concerned with a combination vaccine for use in the protection of poultry against Newcastle disease (ND) comprising a NDV immunogenic subunit or a heterologous vector capable of expressing a NDV immunogenic protein, and a kit comprising the components for such a combination vaccine.

BACKGROUND OF THE INVENTION

Newcastle disease is a viral infection of poultry with a wide geographical distribution causing great economical losses in the poultry industry. Newcastle disease virus (NDV) is the etiologic agent of this disease and represents the prototype virus of the genus Paramyxovirus. Newcastle disease is complicated in that different isolates and strains of the virus may induce enormous variation in the severity of the disease. In general, the younger the chicken the more acute and severe the disease. The infection may take place by either inhalation or ingestion and the infectious form of the virus is spread from one bird to another.

As mentioned above several pathotypes of NDV have been identified, i.e. velogenic, mesogenic and lentogenic. Although these terms refer to results from a laboratory test, the terms are now generally used to describe viruses of high, moderate or low virulence for chickens. The neurotropic velogenic form of disease is caused by highly pathogenic strains of NDV and is characterized by a sudden onset of severe respiratory signs followed by neurological signs. In most cases the infected animals do not survive. Viscerotropic velogenic NDV strains are highly pathogenic and cause high mortality and severe lesions in the gastrointestinal tract. Mesogenic strains of NDV usually cause severe respiratory disease in fully susceptible birds, and in adult birds cause a marked drop in egg production. Lentogenic strains of NDV cause a mild disease characterized by respiratory signs, especially in young fully susceptible birds.

In order to reduce the economic losses due to ND in the commercial poultry industry chickens have been vaccinated against ND. Live vaccines derived from lentogenic and mesogenic strains have been applied routinely, the mesogenic vaccine being suitable only for secondary vaccination. However, also in the lentogenic group there is a considerable range in virulence. NDV strains used as live vaccines include V4, Hitchner B1, F, La Sota (lentogenic), and strain H, Mukteswar, Korearoy and Roakin (mesogenic). The main advantage of live ND vaccines is that these can be administered by inexpensive mass application techniques, such as spray and drinking water application. However, live vaccines may cause severe vaccination reactions, in particular in the respiratory tract after spray vaccination. Because of this, it is important to use extremely mild virus for vaccination, in particular for primary vaccination. However, as a result, multiple applications of vaccines are usually needed.

Inactivated vaccines are administered by injection, generally to older birds. Mostly, these vaccines contain the killed virus mixed with an adjuvant carrier, such as aluminium hydroxide or a water-in-oil emulsion. Viruses used for the preparation of oil-emulsion vaccines include Ulster 2C, Hitchner B1, La Sota, Roakin and various virulent viruses (D. J. Alexander, In Diseases of Poultry, 9th edition 1991, eds. Calnek et al., Iowa State University Press, Ames, Iowa, 496–519).

The commonly used live NDV strains Hitchner B1 and La Sota still cause moderate respiratory vaccination reactions. As a result of this, NDV vaccines based on more mild live strains have been developed, although it is generally accepted that the immunogenicity of the vaccine strains, particular in MDA positive birds, decrease with their virulence. Several of such mild strains have been described in the prior art. U.S. Pat. No. 5,250,298 (University of Delaware) discloses a live, cold-adapted temperature-sensitive mutant of the Hitchner B1 parent strain, designated CaTs. U.S. Pat. No. 5,149,530 (Duphar Int. Res. B.V.) describes the strain NDW derived from the Ulster 2C strain. Furthermore, in U.S. Pat No. 5,188,502 (University of Georgia Research Foundation, Inc.) a naturally attenuated NDV strain isolated from the intestinal tract of a turkey showing no signs of respiratory disease is disclosed. A further mild NDV strain, designated C2, is described in the co-pending U.S. patent application Ser. No. 08/509,911 (AKZO Nobel N.V.).

Recent developments in the genetic engineering technology have enabled the use of a new generation of vaccines based on the expression of immunogenic virus components, the so-called subunits. The main advantage of this kind of vaccine, over the conventional live NDV vaccines based on lentogenic NDV strains is that they do not cause the respiratory vaccination reactions that usually occur after conventional vaccination. Furthermore, no NDV production is necessary with these subunit vaccines and thus the possibility of reversion to virulence of the vaccine virus is decreased.

Vaccines based on either an immunogenic subunit NDV protein or on a heterologous vector capable of expressing an immunogenic NDV protein are disclosed in the prior art. In particular, vaccines based on the expression of the NDV fusion (F) or haemagglutininneuraminidase protein by live viral vectors such as herpes virus of turkeys (HVT) and fowlpox virus (FPV), or by the baculovirus expression system have been described recently (Morgan, R. W. et al., Avian Diseases 36, 858–870, 1992; Boutsnell, M.E.G. et al., Virology 178, 297–300, 1990 and J. Gen. Virology 71, 621–628, 1990; Mori, H. et al., Avian Diseases 38, 772–777, 1994; Nagy, E. et al., Avian Diseases 35, 585–590, 1991).

Local respiratory tract protection is important in preventing initial NDV infection and subsequent disease and in limiting the spread of virus to susceptible chickens via inhalation or ingestion of contaminated feed or drinking water. Generally, conventional live NDV vaccines induce adequate local respiratory protection. Most studies using FPV-NDV vaccines only studied systemic immunity against neurological signs but did not evaluate respiratory immunity. Furthermore, an FPV-NDV/F or FPV-NDV/HN vaccine administered by the ocular route induced only poor systemic protection and no added benefit from immunisation with both recombinant FPV-NDV/F and FPV-NDV/HN could be detected (Edbauer, C. et al., Virology 179, 901–904,1990). In addition, in Morgan et al., Avian Diseases 36, supra; and Avian Diseases 37, 1032–1040, 1993, it was demonstrated that the administration of a live viral vector-based NDV vaccine results in relative low levels of local respiratory protection, in particular in the presence of maternal derived antibodies (MDA) to NDV and a late challenge.

SUMMARY OF THE INVENTION

The present invention provides a NDV combination vaccine which induces enhanced protection against ND both on the local and systemic level of protection.

In particular the present invention involves a combination vaccine for use in the protection of poultry against ND comprising on the one hand a first active component, which is a NDV immunogenic subunit or a heterologous vector capable of expressing a NDV immunogenic protein, and on the other hand a second active component, which is a live NDV vaccine strain. The benefit of said first component if administered as a single component mainly resides in the generation of systemic protection (against mortality and nervous signs such as clonic spasms, muscular tremors, torticollis, opisthotonos and paralysis) in inoculated birds, whereas said second component in that case mainly induces a local protection in the respiratory tract (against multiplication of NDV challenge virus in the tracheas). Surprisingly it has been found in the present invention that the combination vaccine defined herein evokes a synergistic protective immune response, both systemically and locally. As a result the claimed vaccine induces high protection against NDV infection by both mesogenic NDV and neurotropic velogenic NDV strains, even in the presence of maternal derived antibodies.

DETAILED DESCRIPTION OF THE INVENTION

Preferably, the combination vaccine comprises a heterologous vector capable of expressing a NDV immunogenic protein. Such a vector is a microorganism, e.g. a bacterium or virus, or a polynucleotide harbouring the gene encoding the immunogenic NDV protein. The vector is able to express said protein or to replicate in inoculated birds thereby expressing said protein, as a result of which the immunized animal elicits an immune response against the protein. The term "heterologous" indicates that in nature the vector does not harbour the NDV gene.

Live virus vectors are most preferred. Many live virus vectors harbouring genes encoding proteins of avian pathogens have been reported already in the art, in particular virus vectors encoding NDV proteins. Suitable virus vectors for use in the present invention are known to those skilled in the art and include pox viruses, herpes viruses and avian retroviruses.

An example of a suitable pox virus is vaccinia, however Avipox viruses are more preferred because their host range is more restricted. In particular, pigeon pox viruses (PPV) and fowl pox viruses (FPV) are considered to be suitable.

Examples of such suitable PPV and FPV vectors harbouring an immunogenic NDV gene are disclosed in Letellier, C. et al., Archives of Virology 118, 43–56, 1991; Edbauer, C. E. et al., Virology 179, 901–904, 1990; Taylor, J. et al., J. Virology 64, 1441–1450, 1990; Ogawa, R. et al., Vaccine 8, 486–490, 1990; Bournsell, M.E.G. et al., Virology 178, 297–300, 1990 and J. Gen. Virology 71,621–628, 1990; and Boyle, D. B. et al., Virus Research 10, 343–356, 1988.

An example of an avian retroviral vector (avian leukosis virus) harbouring the NDV HN-gene is disclosed in Morrison, T. et al., Microbial Pathogenesis 9, 387–396, 1990.

An even more preferred viral vector to be used in the present invention is HVT (herpes virus of turkeys; see Sondermeyer, P.I.A. et al., Vaccine 11, 349–358, 1993). HVT has several advantages including its proven safety and efficacy against Marek's disease. Furthermore, HVT can be routinely administered to one-day-old chicks. The construction of a HVT-NDV vector harbouring the HN- or F-gene and its efficacy as the single active component in a vaccine is described in Morgan R. W. et al., Avian Diseases 36, 858–870, 1992 and 37, 1032–1040, 1993.

A virus vector as described above can be prepared by conventional recombinant DNA techniques, whereafter host cells infected with the vector virus can be cultured in order to produce sufficient amounts of the vector virus. Subsequently, virus containing cells and/or vector viruses in a purified form can be harvested from the culture followed by the incorporation thereof in a vaccine according to standard methods.

Suitable bacterial vectors to be used herein comprise *E. coli* and several Salmonella species.

Alternatively, the vector is a polynucleotide harbouring the NDV gene operably linked to a promoter, enhancer or other sequences that enable the gene to be expressed in avian cells. In general, the polynucleotide may be a linear DNA molecule. Usually the NDV gene is placed within a bacterial plasmid. Such a vector can be used for DNA-based immunization wherein the polynucleotide is directly transfered in the avian cells by in vivo transfection by methods known for this purpose (Donnelly, J. I. et al., The Immunologist 2, 20–26, 1994).

As an alternative for the heterologous vector defined above, a NDV immunogenic subunit can be incorporated into the vaccine according to the invention. In the case of a subunit vaccine a NDV immunogenic protein is produced in vitro in sufficient amounts such that it can be administered to the animal to be immunized as an active component of the vaccine. The term NDV immunogenic subunit refers to a compound or composition comprising a NDV immunogenic protein essentially free from the NDV (proteinaceous) material with which is normally associated in nature.

In principle, the NDV immunogenic subunit can be purified from the NDV virions by standard biochemical purification techniques although the expression of the subunit by an recombinant DNA expression system is preferred.

In the latter case the NDV immunogenic subunit is expressed by a host cell. A suitable host cell is a cell which can be transformed by a DNA fragment encoding the subunit and which is able to express said subunit.

"Transformation", as used herein, refers to the introduction of a heterologous nucleic acid sequence into a host cell, irrespective of the method used, for example direct uptake or transduction. The heterologous nucleic acid sequence may be integrated into the host genome. For expression the heterologous DNA fragment is provided with appropriate expression control sequences that are compatible with the designated host and can regulate the expression of the inserted nucleic acid sequence.

The host cell can be of prokaryotic origin, e.g. bacterial expression systems derived from *E. coli, Bacillus subtilis* or *Pseudomonas* species.

The host cell preferably is of eukaryotic origin such as a yeast, e.g. *Saccharomyces cerevisiae* or a higher eukaryotic cell such as an insect, plant or mammalian cell, including HeLa cells and Chinese hamster ovary (CHO) cells. Insect cells include the Sf9 cell line of *Spodoptera frugiperda* (Luckow et al., Biotechnology 6, 47–55, 1988). Information with respect to the cloning and expression of the NDV immunogenic subunit in eukaryotic cloning systems can be found in Esser, K. et al. (Plasmids of Eukaryotes, Springer-Verlag, 1986).

Alternatively, a suitable host cell is a cell which is susceptible for infection by a recombinant virus harbouring a DNA fragment encoding the NDV immunogenic subunit. In the virus the heterologous DNA fragment is inserted into a non-essential region of the virus, i.e. a region which can be used for the incorporation of said DNA fragment without disrupting essential functions of the virus such as those necessary for infection or replication of the virus.

To obtain large quantities of the NDV immunogenic subunit the preferred expression system is the baculovirus expression system (BVES). In this system insect cells like Spodoptera furgiperda (Sf, IPLB-Sf21) cells are kept in cell culture as host for a baculovirus, like an Autographa californica nuclear polyhedrosis virus (AcNPV). Some of the genes in AcNPV are expressed to high levels, but are non-essential to the vital infection-cycle. These genes are the target for homologous recombination in transfected cells between a baculo-transfer plasmid like pAcAS3 and wild-type (wt) AcNPV DNA. In pAcAS3 (J. Vlak et al., Virology 179, 3 12–320, 1990) heterologous genes are inserted downstream of the p10 promoter instead of the non-essential p10 gene, surrounded by sequences of wt AcNPV that target the recombination process. To facilitate screening for recombinants, pAcAS3 also contains the LacZ gene, causing recombinant plaques to turn blue upon addition of X-gal to the medium.

The construction of recombinant baculoviruses harbouring the NDV F- or HN gene and the expression thereof in insect cells has been reported in the prior art, e.g. by Kamiya, N. et al., Virus Research 32, 373–379, 1994; Murakami, Y. et al., Virus Research 33, 123–137, 1994; Niikura, M. et al., Virus Research 20, 31–43, 1991; Mori, H. et al., Avian Diseases 38, 772–777, 1994; Nagy, E. et al., Virology 176, 426–438, 1990 and Avian Diseases 35, 585–590, 1991.

Cosset, F-L et al., Virology 185, 862–866, 1991 describe the preparation of a NDV subunit vaccine based on a cell line constitutively expressing the HN protein.

In the present invention the host cells defined above can be cultured under conditions which are favourable for the expression of the NDV immunogenic subunits. Vaccines may be prepared using samples of the crude culture, host cell lysates, host cell extracts or culture supernatants, although in another embodiment more purified subunits may be prepared depending on its intended use. In order to purify the proteins produced, host cells expressing the subunits are cultured in an adequate volume and the proteins produced are isolated from such cells or from the medium if the proteins are excreted. Proteins excreted into the medium can be isolated and purified by standard techniques, e.g. salt fractionation, centrifugation, ultrafiltration, chromatography, gel filtration immunoprecipitation or immunoaffinity chromatography, whereas intracellular proteins can be isolated by first collecting said cells, disrupting the cells, for example by sonication or by other mechanically disruptive means such as French press, followed by separation, if desired, of the proteins from the other intracellular components. Cell disruption could also be accomplished by chemical (e.g. EDTA treatment) or enzymatic means such as lysozyme digestion.

As the second active component of the present invention any of the well-known live NDV lentogenic vaccine strains can be used. Such strains include Hitchner B1 and La Sola vaccine strains.

Detailed information concerning live NDV vaccine strains, vaccine production and vaccine administration are disclosed for example by Allan et al, FAO Animal Production and Health Series No. 10, FAO, Rome, 1978 and D. L. Alexander, In: Diseases of Poultry, 9th edition 1991, eds. Calneck et al., Iowa State University Press, Amer., Iowa, 496–519.

A problem associated with the use of live ND vaccines is the presence of maternal derived NDV antibodies in commercial chickens which interfere with the establishment of protection after vaccination. This problem can be overcome by using relatively virulent NDV vaccine strains. A disadvantage of such more virulent live NDV vaccines is, however, that they cause or contribute to respiratory disease resulting in a decreased performance of the chickens or even mortality in young chicks.

Consequently, a particular preferred embodiment of the present invention is a combination vaccine wherein the live NDV vaccine strain is a mild lentogenic NDV strain. Such a combination vaccine induces no or only minor respiratory vaccination reactions and at the same time evokes an enhanced protective immune response. With mild lentogenic vaccine strains are meant vaccine strains with a Vaccinal Reaction Index (VRI 1 and VRI 2) smaller than 2. VRI's are inter alia based on weight loss due to vaccination and range from 0 to 10 (van Eck, J.H.H. et al., Avian Pathology 20, 497–507, 1991). Examples of such mild vaccine strains are NDV strains C2 (CNCM deposit No. 1–1614), CaTs (U.S. Pat. No. 5,250,298), the naturally attenuated turkey strain disclosed in U.S. Pat. No. 5,118,502, and NDW (U.S. Pat. No. 5,149,530), the C2 strain being most preferred.

The NDV immunogenic subunit or protein to be used herein is a protein component of the ND virus which is able to induce a protective immune response in poultry and includes the F-, HN-, matrix (M) and nucleoprotein (NP) proteins.

In particular, the preferred NDV immunogenic subunit or protein is the F- or HN-protein. Examples of these virus components and the genes encoding said components are disclosed in several of the documents mentioned above.

A very advantageous combination vaccine according to the present invention comprises the live NDV C2 strain and the HVT-NDV/F vector.

Although, the vaccine according to the present invention may be used effectively in chickens, other poultry such as turkeys, guinea fowl and partridges may also be successfully vaccinated with the vaccine. Chickens include broilers, reproduction stock and laying stock.

Although preferred, both the active components of the combination vaccine do not necessarily have to be administered in a mixed form. The way of administration for each component may depend on the specific properties of each of the components. For example, the live NDV vaccine strains are preferably administered by the inexpensive mass application techniques commonly used for ND vaccination, such as by spray or by drinking water. However, administration by injection for such vaccines is also contemplated. The NDV immunogenic subunit expressed by for example a baculovirus or a heterologous vector defined above, for example derived from HVT or FPV, is usually administered parenterally. However, other routes of vaccination are also contemplated, such as in ovo, as long as the specific active component is able to evoke a protective immune response after administration. The advantages of the present invention can also be achieved if the components of the combined vaccine are administered to the birds separated by a small interval of time, e.g. by an interval of about 24 hours, preferably 8 hours. For example, the advantageous effect of the combination vaccine can also be obtained if one of the components, e.g. the HVT vector described above, is administered in ovo just before hatch, and the live NDV vaccine strain is administered immediately after hatch, e.g. at one-day-old.

The vaccine according to the invention comprises an effective dosage of the active components, i.e. an amount of immunising active component that will induce immunity in the vaccinated birds against challenge by a virulent ND virus. Immunity is defined herein as the induction of a significant higher level of protection in a population of birds after vaccination compared to an unvaccinated group.

Typically, the live NDV vaccine strain can be administered in a dose of $10^{3.0}$–$10^{8.0}$ embryo infectious doses$_{50}$ (EID$_{50}$) per animal, preferably in a dose ranging from $10^{5.0}$–$10^{7.0}$ EID$_{50}$. HVT based vectors can be administered in an amount of 10–10.000 pfu, preferably 100–1500 pfu, whereas FPV vectors are usually effective if administered in an amount of $10^{2.0}$–$10^{5.0}$TCID$_{50}$. Effective baculovirus expressed subunit vaccines normally are derived from $10^{5.0}$–$10^{8.0}$ cells.

The combination vaccine according to the invention can be administered to the birds directly after hatch, i.e. from one-day-old on. The vaccine can be used as a primary vaccination, if desired followed by one or more secondary vaccinations. The combined vaccine is also suited for incorporation in vaccination programmes that also involve the use of a monovalent NDV vaccine in live or inactivated form.

As an example, broilers may be vaccinated at one-day-old followed by a secondary immunization at 10–21 days. Laying stock or reproduction stock may be vaccinated at 1–10 days followed by booster vaccinations on 26–38 days and 16–20 weeks.

The invention also involves multivalent vaccines comprising, in addition to the two active components defined above, a vaccine comprising one or more immunogens derived from other pathogens infectious to poultry.

Preferably, the combination vaccine additionally comprises one or more vaccine strains of infectious bronchitis virus (IBV), infectious bursal disease virus (IBDV), chicken anemia agent (CAA) or reovirus.

The vaccine according to the invention can be prepared and marketed in the form of a suspension or in a lyophilised form and additionally contains a pharmaceutically acceptable carrier or diluent customarily used for such active components. Carriers include stabilisers, preservatives and buffers. Suitable stabilisers are, for example SPGA, carbohydrates (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

If desired, the vaccine according to the invention may contain an adjuvant. Suitable compound or compositions for this purpose include aluminium hydroxide, -phosphate, or -oxide, oil-in-water or water-in-oil emulsion based on, for example a mineral oil, such as Bayol F® or Marcol 52® or a vegetable oil such as vitamin E acetate, and saponins.

The invention herein also contemplates a kit format which comprises a packaged multicontainer unit having containers of each active component as defined above. The kit may also have a container with a carrier or diluent for one or both of the active components.

EXAMPLE 1

Efficacy of combined administration of HVT-NDV/F vector and a live NDV vaccine strain The HVT-NDV/F vector was prepared as described in Morgan, R. W. et al., Avian Diseases 36, 858–870, 1992 and Sondermeyer, P. J. A. et al., Vaccine 11, 349–358, 1993.

HVT-NDV/F was propagated on primary chicken embryo fibroblasts (CEF) prepared from 10 day-old embryonated specific pathogen-free eggs. Cells were maintained in a combination of Glasgow's and Eagle's modified minimum essential medium supplemented with 5% fetal calf serum and a cocktail of antibiotics. CEF were seeded in roller bottles at a density of approx. $6\times10^5$ cells/cm$^2$, infected with HVT-NDV-F at an moi of $\leq 0.01$ pfu/cell and incubated at 37° C. for 48–72 h. When cultures reached approx. 80% cytopathic effect, infected cells were harvested using trypsin, spun and resuspended in freezing media. Aliquots of infected cells were stored in sealed glass arepules in the gas phase of liquid nitrogen.

The live NDV vaccine was prepared from the mild NDV vaccine strain C2 (deposited at the CNCM of the Institute Pasteur, 25 Rue du Docteur Roux, Paris, France under accession No. 1–1614

NDV C2 X+4 was diluted to contain approximately 3–4 logs of virus per 0.1 ml and was inoculated into 200 10–12 day-old SPF embryos. Embryos were placed at 37° C. Four days post-inoculation the embryos were candled and all live embryos were placed at 4° C. for 2 hours. Allantoic fluid was then harvested. A total of 1340 ml of allantoic fluid was mixed with 660 ml of stabilizer and 20 ml of Gentocin. This was mixed for 15 minutes then filled into 10 ml glass vials, 2 ml per vial. The vials were then freeze-dried.

Two groups of each 30 one-day-old commercial broiler chickens were inoculated with the NDV-C2 strain via oculo-nasal route.

Two groups of each 30 one-day-old commercial broiler chickens were inoculated with the HVT-NDV/F strain via intramuscular route.

Four groups of each 30 one-day-old commercial broiler chickens were inoculated with the HVT-NDV/F strain via the intramuscular route and with the NDV-C2 strain via the oculo-nasal route. At two and five weeks of age 2 SPF control chickens of the same age were added to each challenge group.

Per inoculum one group of chickens was challenged with the NDV Hefts 33/56 strain via the intramuscular route. These chickens were monitored over a period of twelve days for the occurrence of clinical signs of Newcastle Disease and/or mortality.

The other groups were challenged with the NDV Beaudette strain, via the oculo-nasal route. Six days post challenge these chickens were sacrificed and their tracheas were removed for virus re-isolation.

Blood samples were collected at one-day of age for determination of antibodies to NDV in the HI-test (the average HI-titre was $10^{6.4}$). In the sera from the five-week-old SPF chickens no antibodies to NDV could be detected.

Chickens were vaccinated with:

| | | |
|---|---|---|
| NDV-C2: | 0.1 ml per chicken | (7.6 log$_{10}$ EID$_{50}$ per dose) |
| HVT-NDV/F: | 0.2 ml per chicken | (±1200 PFU per dose) |

Chickens were challenged with:

| | | |
|---|---|---|
| NDV Beaudette:. | 0.2 ml per chicken | (7.6 log$_{10}$ ELD$_{50}$ per dose) |
| NDV Herts 33/56 | 0.2 ml per chicken | (7.6 log$_{10}$ ELD$_{50}$ per dose) |

Determination of systemic protection

For a period of twelve days post challenge with the NDV Hefts strain all chickens were observed daily for the occurrence of mortality or clinical evidence of Newcastle Disease. The data were recorded daily. The score system was as follows:

0: no occurrence of clinical evidence of Newcastle Disease

1: occurrence of clinical evidence of Newcastle Disease central nervous signs like:
clonic spasm
muscular tremors
torticollis
opisthotonos
paralysis of legs, occasionally of wings 2: mortality due to the NDV challenge.

Determination of local protection

All chickens challenged with the NDV-Beaudette strain were sacrificed at six days post challenge and their tracheas were removed. All tracheas were stored frozen in tryptose 2.5% broth at −70° C. until virus re-isolation was carded out.

Per trachea sample 8–10 eggs were inoculated via the allantoic cavity. The eggs were incubated for eight days at +37° C. in an egg incubator with rocking. Embryo mortality occurring after 24 hours post-inoculation was considered to be due to NDV replication.

The local and systemic protection results obtained at two and five weeks post vaccination are shown in Table 1.

TABLE 1

| Inoculum | Systemic protection Percentage of protection against NDV Herts 33/56 at weeks post administration | | Local protection Percentage of protection against NDV Beaudette at weeks post administration | |
|---|---|---|---|---|
|  | 2 | 5 | 2 | 5 |
| NDV-C2 strain | 73 | 13 | 27 | 13 |
| HVT-NDV/F strain | ND | 29 | ND | 20 |
| NDV-C2 + HVT-NDV/F combination | ND | 87 | ND | 75 |
| None (SPF chickens) | 0 | 0 | 0 | 0 |

ND = not done

The live NDV C2 vaccine induced only partial protection, both locally and systemically, in the presence of high levels of MDA. Also the monovalent HVT-NDV/F vaccine induced poor local (and systemic) protection under these circumstances.

Unexpected was the fact that after administration of the NDV-C2 and HVT-NDV/F combination, when compared to the single administrations, both the local and systemic protection improved exceptionally. This synergistic effect surely makes the combination a good vaccine candidate for vaccination, in particular of one-day-old commercial broilers, against NDV.

EXAMPLE 2

Efficacy of combined administration of HVT-NDV/HN or FPV-NDV/F and live NDV vaccine strain C2 or VG/GA Both the vaccines comprising the mild lentogenic NDV strains C2 or VG/GA were prepared in a manner similar to the NDV C2 based vaccine described in Example 1. NDV strain VG/GA is described in U.S. Pat. No. 5,118,502 (ATCC no. VR 2239). The HVT-NDV/HN vector vaccine was prepared as described by Morgan et al. and Sondermeyer et al.(Example 1).

The NDV F gene as described in Example 1 was inserted into the non-essential region in the Barn-HI J fragment of the FPV (fowlpox virus) genome as disclosed in international application WO 90/02191. An expression cassette containing the F-gene under control of a vaccinia promoter and a lacZ marker gene was recombined in vivo by transfecting the DNA into FPV infected chicken cells. Recombinants were identified by bluo-gal staining and purified to homogeneity following successive rounds of plaque purification. Expression of the F-gene was confirmed by fluorescence staining and immunoprecipitation with NDV specific antisera.

140 commercial broiler chickens were assigned randomly to seven groups so that each group contained 20 chickens. Another 20 one-day-old hatch mates were bled and sera were examined for the presence of antibodies to NDV. At one day of age the chickens in group 1 were inoculated with the NDV VG/GA strain, the chickens in group 2 were inoculated with the HVT-NDV/HN strain, the chickens in group 3 were inoculated with both the NDV VG/GA strain and HVT-NDV/HN strain, the chickens in group 4 were inoculated with the NDV-C2 strain, the chickens in group 5 were inoculated with the FPV-NDV/F strain, the chickens in group 6 were inoculated with both the NDV-C2 strain and FPV-NDV/F strain and the chickens in group 7 were not inoculated and served as controls. At 14 and 31 days of age blood samples were collected from all chickens individually and sera were examined for the absence/presence of antibodies to NDV. At 31 days of age all chickens were subjected to a challenge with the NDV Herts strain. For a period of 10 days post challenge chickens were observed daily for the occurrence of mortality.

Treatment 20 one-day-old chickens in group 1 and group 3 were inoculated each with 0.1 ml of NDV VG/GA-GA containing 5.2 $\log_{10}$ EID$_{50}$ of infectious NDV particles, via the ocular route.

20 one-day-old chickens in group 4 and group 6 were inoculated each with 0.1 ml of NDV C2 containing 7.2 $\log_{10}$ EID$_{50}$ of infectious NDV particles, via the ocular route.

20 one-day-old chickens in group 2 and group 3 were inoculated each with 0.2 ml of HVT-NDV-HN containing 838 PFU of infectious HVT particles, via the intramuscular route.

20 one-day-old chickens in group 5 and group 6 were inoculated each with 0.2 ml of FPV-NDV/F containing 45000 PFU of infectious FPV particles, via the subcutaneous route.

At 31 days of age the chickens were challenged with 0.2 ml of NDV strain Herts containing 7.4 $\log_{10}$ EID$_{50}$ of infectious NDV particles, via the intramuscular route.

Observation for clinical signs of disease

After challenge with the NDV Herts strain the chickens were observed daily for occurrence of mortality for a period of 10 days.

Serology

At 14 and 35 days of age blood samples were collected from all chickens individually from the wing vein.

Serum samples were examined for antibodies to NDV in the NDV HI-test according to standard procedures.

The efficacy of both the monovalent- and combination vaccines are shown in Table 2A and 2B.

TABLE 2A

Serology results:

| Vaccine | Mean log$_2$ antibody titre to NDV at 31 days post inoculation |
| --- | --- |
| NDV strain VG/GA | 2.1 ± 1.8 |
| HVT-NDV/HN | 2.1 ± 1.8 |
| NDV strain VG/GA + HVT-NDV/HN | 6.7 ± 1.1 |
| Controls | 0.1 ± 0.2 |

TABLE 2B

Percentage of protection against an intramuscular NDV Herts challenge at 31 days of age

| Vaccine | Percentage of protection based on the number of dead chickens |
| --- | --- |
| NDV strain C2 | 53% |
| FPV-NDV/P | 15% |
| NDV strain C2 + FPV-NDV/F | 75% |
| Controls | 0% |

Table 1A shows that both the mild lentogenic NDV VG/GA strain and the HVT-NDV/HN vaccine strain induced only a moderate HI-antibody response, whereas the combination vaccine induced a high synergistic immune response. Similarly, the protection afforded by the combination vaccine comprising both the mild lentogenic. NDV C2 strain and the FPV-NDV/F vector was higher than the sum of the protection induced by the monovalent vaccines.

We claim:

1. A combination vaccine for the protection of poultry against Newcastle Disease (ND), comprising (1) a Newcastle Disease Virus(NDV) protein immunogenic subunit or a heterologous vector capable of expressing an NDV immunogenic protein, and (2) a live NDV mild lentogenic vaccine strain.

2. The combination vaccine according to claim 1, wherein the heterologous vector is a live virus vector.

3. The combination vaccine according to claim 1, wherein the NDV immunogenic subunit is the expression product of a bacterial or insect cell expression system.

4. The combination vaccine according to claim 3, wherein the immunogenic subunit is the expression product of a recombinant baculovirus.

5. The combination vaccine according to claim 2, wherein the live vector virus is herpes virus of turkeys (HVT) or fowlpox virus (FPV).

6. The combination vaccine according to claim 1, wherein component (1) is a fusion (F) or a hemagglutinin-neuraminidase (HN) protein.

7. The combination vaccine according to claim 1, wherein the mild lentogenic NDV strain is the C2 strain, deposited with the CNCM of the Institute Pasteur, Paris, France under accession no. 1–1614.

8. A vaccination kit for immunizing poultry against Newcastle disease (ND), which kit comprises the following components:

(a) a Newcastle disease virus (NDV) immunogenic subunit or a heterologous vector capable of expressing an NDV immunogenic protein; and (b) a live NDV mild lentogenic vaccine strain.

9. The kit according to claim 8, further comprising a carrier or diluent for either or both of components (a) and (b).

10. The kit according to claim 9, wherein the carrier or diluent is an adjuvant.

11. A method for the prevention of Newcastle disease (ND) in poultry, comprising the combined administration of an effective amount of (1) a vaccine comprising a Newcastle disease virus (NDV) immunogenic subunit or a heterologous vector capable of expressing an NDV immunogenic protein, and (2) a vaccine comprising a live NDV mild lentogenic vaccine strain.

12. A method for the prevention of Newcastle disease (ND) in poultry, comprising administering an effective amount the combination vaccine of claim 1.

* * * * *

UNITED STATES PATENT AND TRADEMARK OFFICE
CERTIFICATE OF CORRECTION

PATENT NO. : 5,733,556
DATED : March 31, 1998
INVENTOR(S) : Carla C. Schrier and Heinrich D. Lutticken It is certified that error appears in the above-indentified patent and that said Letters Patent is hereby corrected as shown below:

Column 7, line 7, delete "$10^{3.0}$ $10^{8.0}$" and replace with -- $10^{3.0}$ - $10^{8.0}$ --; and line 10, delete "10-10.000" and replace with -- 10 - 10,000 --.

Claim 12, last line, after "amount", insert -- of --.

Signed and Sealed this

Eighteenth Day of August, 1998

Attest:

BRUCE LEHMAN

*Attesting Officer*  *Commissioner of Patents and Trademarks*